United States Patent
Kollander (10) Patent No.: US 12,188,744 B2
(45) Date of Patent: Jan. 7, 2025

(54) TOURNIQUET HOLDER

(71) Applicant: Jason Kollander, Wasilla, AK (US)

(72) Inventor: Jason Kollander, Wasilla, AK (US)

(*) Notice: Subject to any disclaimer, the term of this patent is extended or adjusted under 35 U.S.C. 154(b) by 346 days.

(21) Appl. No.: 17/878,133

(22) Filed: Aug. 1, 2022

(65) Prior Publication Data
US 2023/0145980 A1 May 11, 2023

Related U.S. Application Data (60) Provisional application No. 63/228,188, filed on Aug. 2, 2021.

(51) Int. Cl.
| | |
|---|---|
| *F41C 27/00* | (2006.01) |
| *A61B 17/132* | (2006.01) |
| *A61B 50/20* | (2016.01) |

(52) U.S. Cl.
CPC .......... *F41C 27/00* (2013.01); *A61B 17/1322* (2013.01); *A61B 50/20* (2016.02)

(58) Field of Classification Search
CPC .... F41C 7/00; F41C 7/02; F41C 7/025; F41C 7/04; F41C 7/06; F41C 7/11; F41C 7/12; F41C 33/001; F41C 33/002; F41C 33/007; F41C 27/00; F41C 27/04; F41C 27/06; F41C 27/16; F41C 27/18; F41C 27/20; F41C 27/22; F41C 23/02; A61B 17/132; A61B 17/1322; A61B 17/1325; A61B 17/1327; A61B 17/135; A61B 17/1355; A61B 50/20
USPC ....................................................... 606/203
See application file for complete search history.

(56) References Cited

U.S. PATENT DOCUMENTS

| | | | | |
|---|---|---|---|---|
| 3,190,444 | A * | 6/1965 | Kelson ............... | A61B 17/1322 206/370 |
| 5,121,564 | A * | 6/1992 | Story ..................... | F41C 27/00 224/931 |
| 5,685,103 | A * | 11/1997 | Wiggins ................. | F41A 23/18 248/230.8 |
| 5,771,622 | A * | 6/1998 | Koziuk ................... | F41C 27/00 42/74 |
| 5,792,173 | A * | 8/1998 | Breen .................. | A61B 17/135 606/1 |
| 9,333,128 | B2 * | 5/2016 | Catrone ................... | A45F 3/00 |
| 2011/0016764 | A1 * | 1/2011 | Cales ..................... | F41C 23/14 42/90 |

(Continued)

*Primary Examiner* — Kankindi Rwego
(74) *Attorney, Agent, or Firm* — Kevin Keener; Keener and Associates (57) ABSTRACT

Provided is a tourniquet holder comprising a mounting base adapted to be operationally engaged with a handguard of an associated weapon, a first tang, a second tang, and an elongated retention strap. The mounting base has a substantially flat plate defining a first base face and a second base face, one or more fastener apertures, and one or more retention slots. The first tang extends in a direction substantially normal to the first base face. The second tang extends in a direction substantially normal to the first base face. The first tang and the second tang define therebetween a margin adapted to accommodate therein an associated tourniquet. The elongated retention strap passes through the one or more retention slots, has a first end and a second end that are selectably engagable with one another to define a loop adapted to retain therein the associated tourniquet.

10 Claims, 13 Drawing Sheets

(56) References Cited

U.S. PATENT DOCUMENTS

| | | | |
|---|---|---|---|
| 2011/0029009 A1* | 2/2011 | Dietl | F41C 27/00 40/672 |
| 2011/0168747 A1* | 7/2011 | Scott | F41C 33/002 224/150 |
| 2014/0027480 A1* | 1/2014 | Van Heusen | A45F 5/02 224/191 |
| 2016/0135575 A1* | 5/2016 | Solomon | A45F 5/02 224/235 |
| 2016/0265873 A1* | 9/2016 | Schuman | F41C 33/002 |
| 2021/0054965 A1* | 2/2021 | Wong | A45F 3/16 |
| 2021/0278170 A1* | 9/2021 | Bernaz | F41C 33/04 |

* cited by examiner

TOURNIQUET HOLDER

CROSS-REFERENCE TO RELATED APPLICATIONS

This application claims the benefit of U.S. Provisional Application No. 63/228,188, filed Aug. 2, 2021.

BACKGROUND

A tourniquet is a device for stopping the flow of blood through a vein or artery, typically by compressing a limb with a cord or tight bandage. Tourniquets are important first aid equipment where there is a substantial risk of injury resulting in vein or artery damage and subsequent blood loss.

There is predictable potential for such injury in situations where there are deployed weapons which, when used, cause physical injury to the target. Such weapons may include those common to hunting, fishing, military applications, and police applications. As a consequence, the weapon users may desire to have ready access to and the ability to readily deploy a tourniquet.

Therefore, it remains desirable to provide apparatus, means, methods or some combination thereof to provide a weapon user with ready access to and the ability to readily deploy a tourniquet.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

Accordingly, the present subject matter is directed to a tourniquet holder that substantially obviates one or more problems resulting from the limitations and deficiencies of the related art.

In accordance with a first non-limiting embodiment of the present invention, there is provided a tourniquet holder comprising a mounting base adapted to be operationally engaged with a handguard of an associated weapon, said mounting base having a substantially flat plate defining a first base face, and a second base face facing oppositely from said first base face, said second base face offset from said first base face by a base thickness, said plate further having a first base side edge and a second base side edge opposite said first base side edge and offset from said first base side edge by a base width, said plate further having a base top edge and a base bottom edge offset from said base top edge by a base height; one or more fastener apertures adapted to operationally engage with a mechanical faster, each said mechanical fastener being further adapted to operationally engage with said handguard, one or more retention slots; and a first tang extending in a direction substantially normal to said first base face; a second tang extending in a direction substantially normal to said first base face; wherein said first tang and said second tang define therebetween a margin adapted to accommodate therein an associated tourniquet; and an elongated retention strap passing through said one or more retention slots, said elongated retention strap having a first end and a second end, said second end being selectably engagable with said first end to selectably define a loop, said loop being adapted to retain therein said associated tourniquet.

Also provided is a method for using a tourniquet holder comprising providing the above referenced first embodiment of a tourniquet holder; providing a weapon having a handguard; providing a tourniquet; engaging said mounting base with the handguard; and using said retention strap to retain said tourniquet.

It is to be understood that the foregoing general description and the following detailed description of the present subject matter are merely exemplary and explanatory in nature. As such, the foregoing general description and the following detailed description should not be construed to limit the scope of the appended claims in any sense.

BRIEF DESCRIPTION OF THE DRAWINGS

Various exemplary embodiments of the present subject matter will be described in detail, wherein like reference numerals refer to identical or similar components, with reference to the following figures, wherein.

Throughout the figures, the same parts are denoted using the same reference characters so that, as a general rule, they will only be described once.

DETAILED DESCRIPTION

The claimed subject matter is now described with reference to the drawings. In the following description, for purposes of explanation, numerous specific details are set forth in order to provide a thorough understanding of the claimed subject matter. It may be evident, however, that the claimed subject matter may be practiced with or without any combination of these specific details, without departing from the spirit and scope of this invention and the claims.

Figure 1:
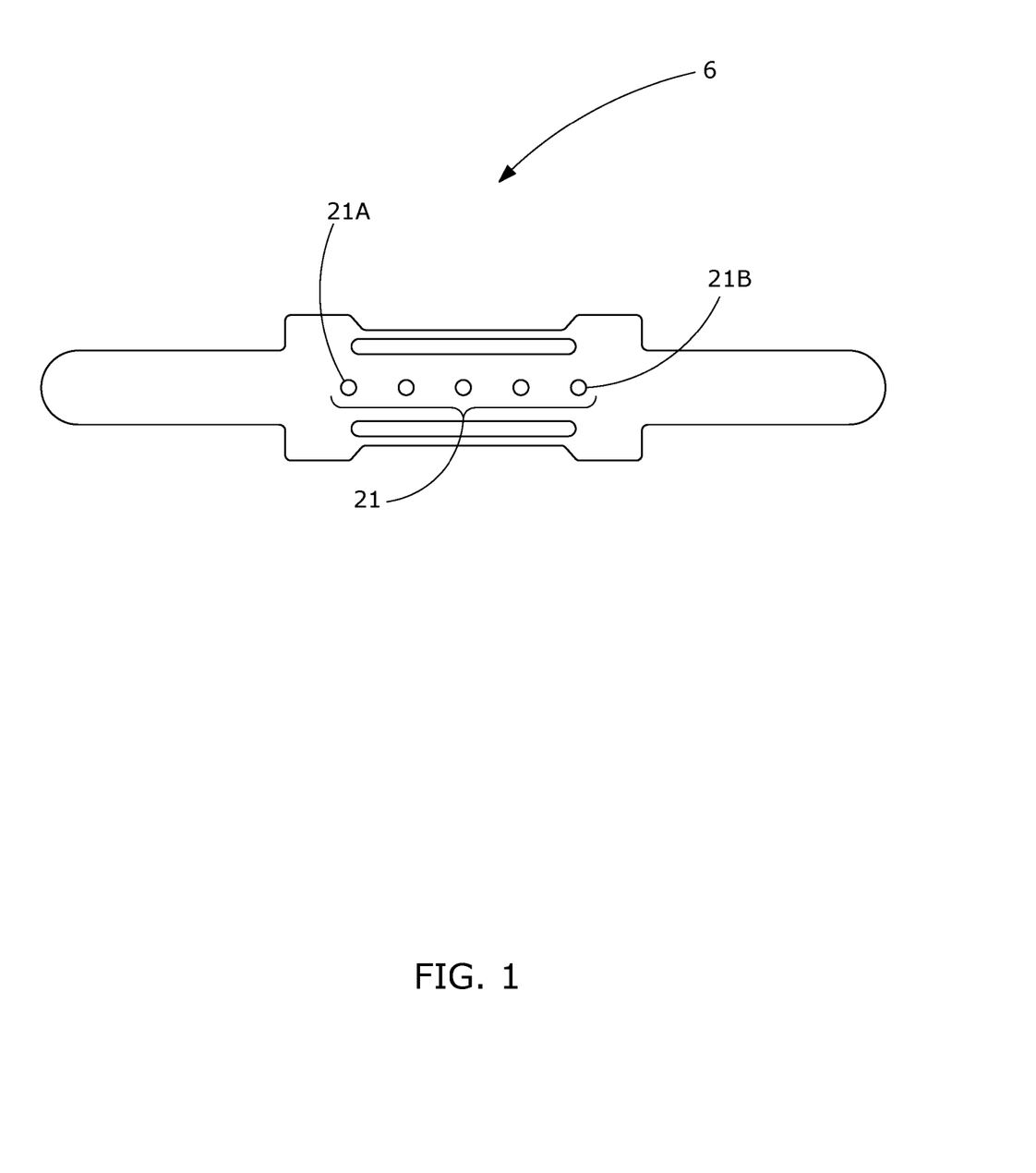
FIG. 1 is a top view of a blank for a tourniquet holder, according to a first embodiment thereof.

An illustrative first embodiment of a blank 6 usable to form the tourniquet holder 10 (see FIGS. 2-3) is seen in FIG. 1. The blank 6 may be a thin sheet of metal or polymer that may then be bent or otherwise subsequently proceed to form the tourniquet holder 10. In some non-limiting embodiments, the blank 6 is cut or stamped from sheet metal, such as and without limitation, from stainless steel.

Figure 2:
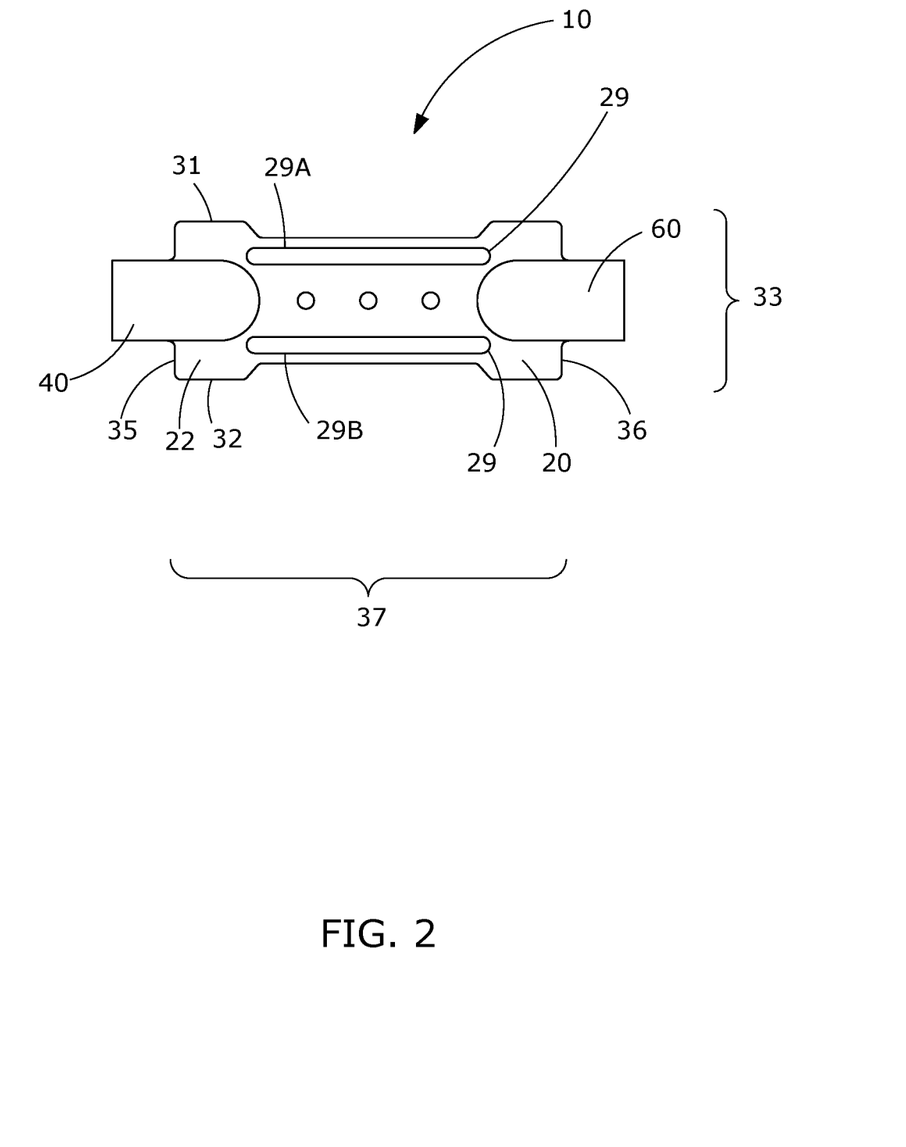
FIG. 2 is a top view of the first embodiment of a tourniquet holder formed from the blank of FIG. 1 with the retention strap removed for visibility.
Figure 3:
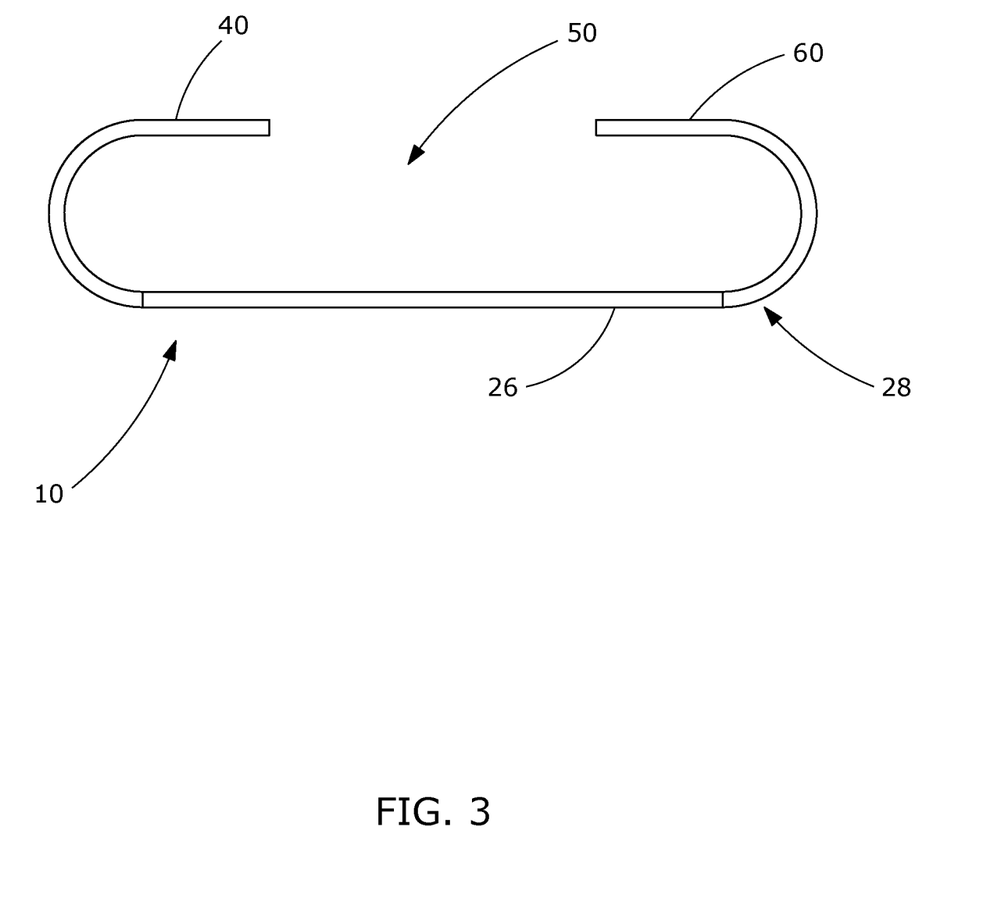
FIG. 3 is a front view of the first embodiment of a tourniquet holder of FIG. 2.
Figure 4:
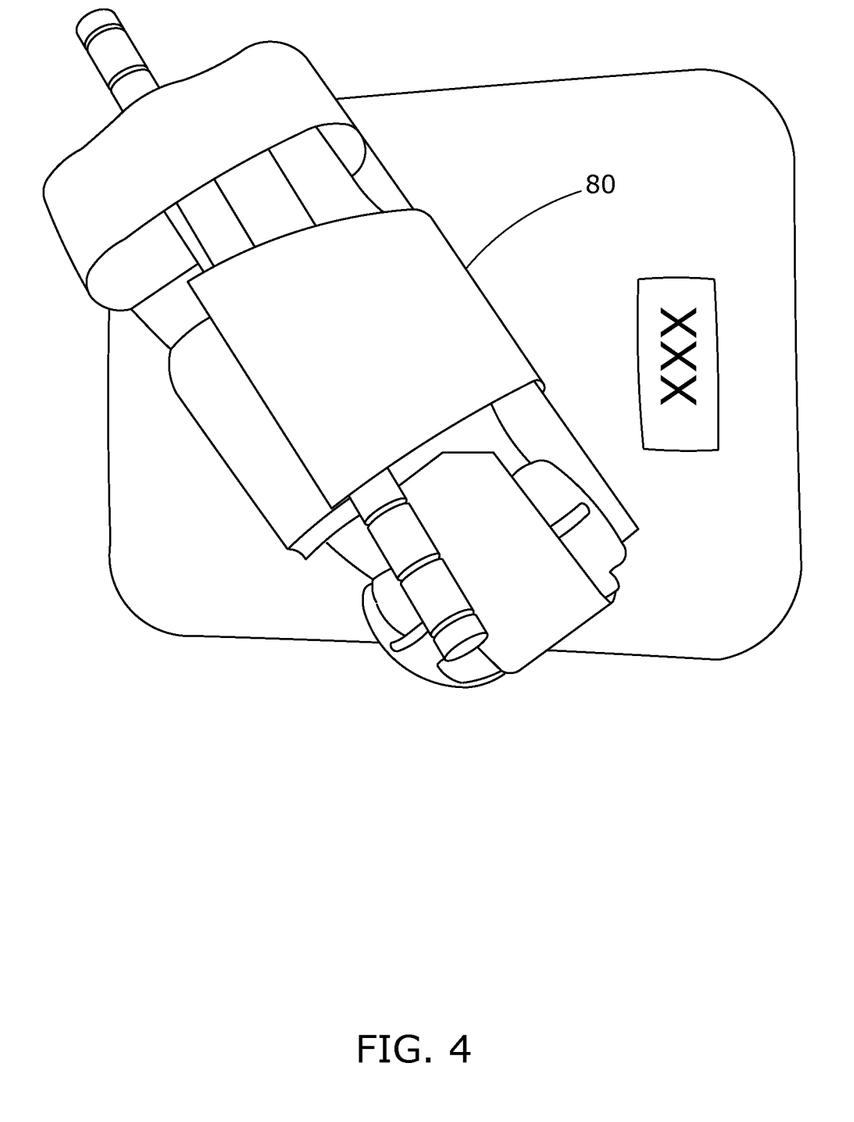
FIG. 4 is a view of a second embodiment of a tourniquet holder with the retention strap and an associated tourniquet shown on a scale being massed.
Figure 5:
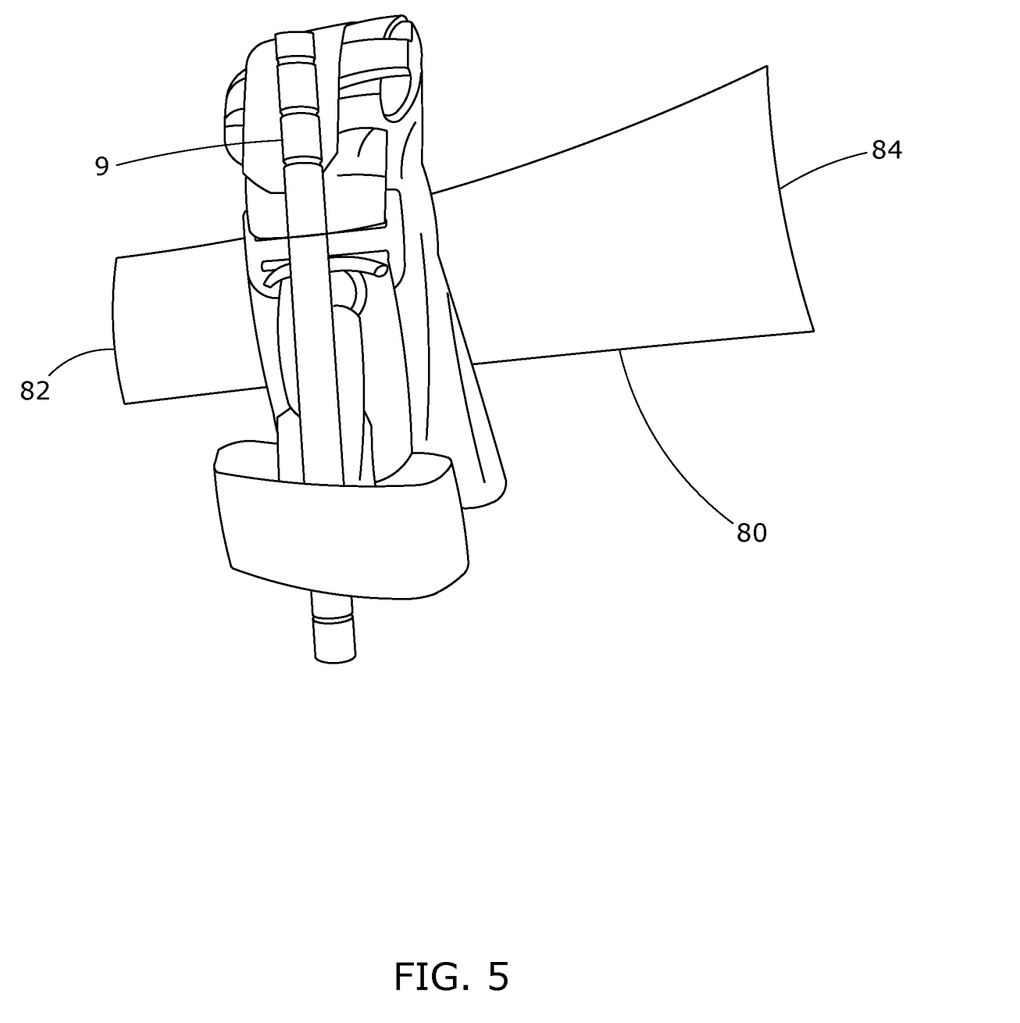
FIG. 5 is a view of the second embodiment of a tourniquet holder of FIG. 4 with the retention strap open and an associated tourniquet.
Figure 6:
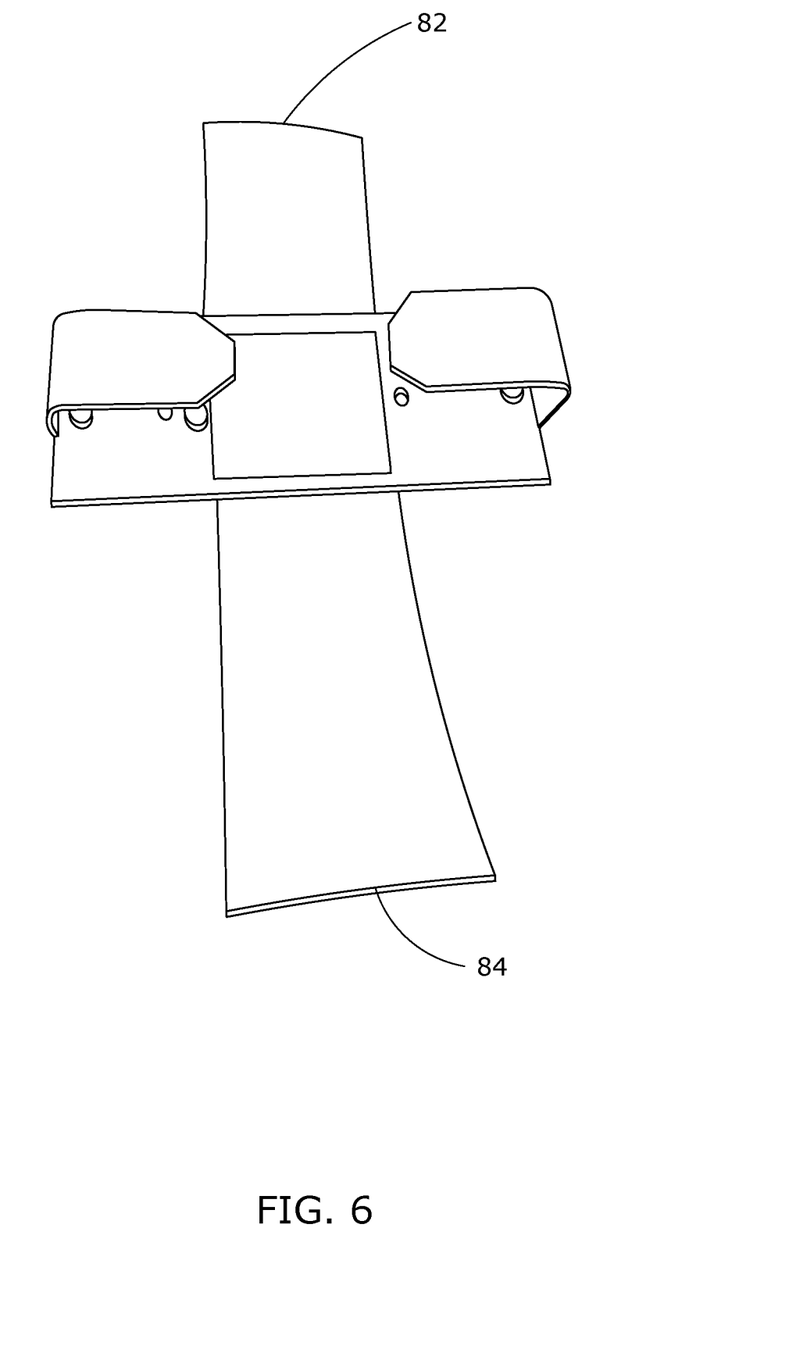
FIG. 6 is a view of the second embodiment of a tourniquet holder of FIG. 4 with the retention strap open.
Figure 7:
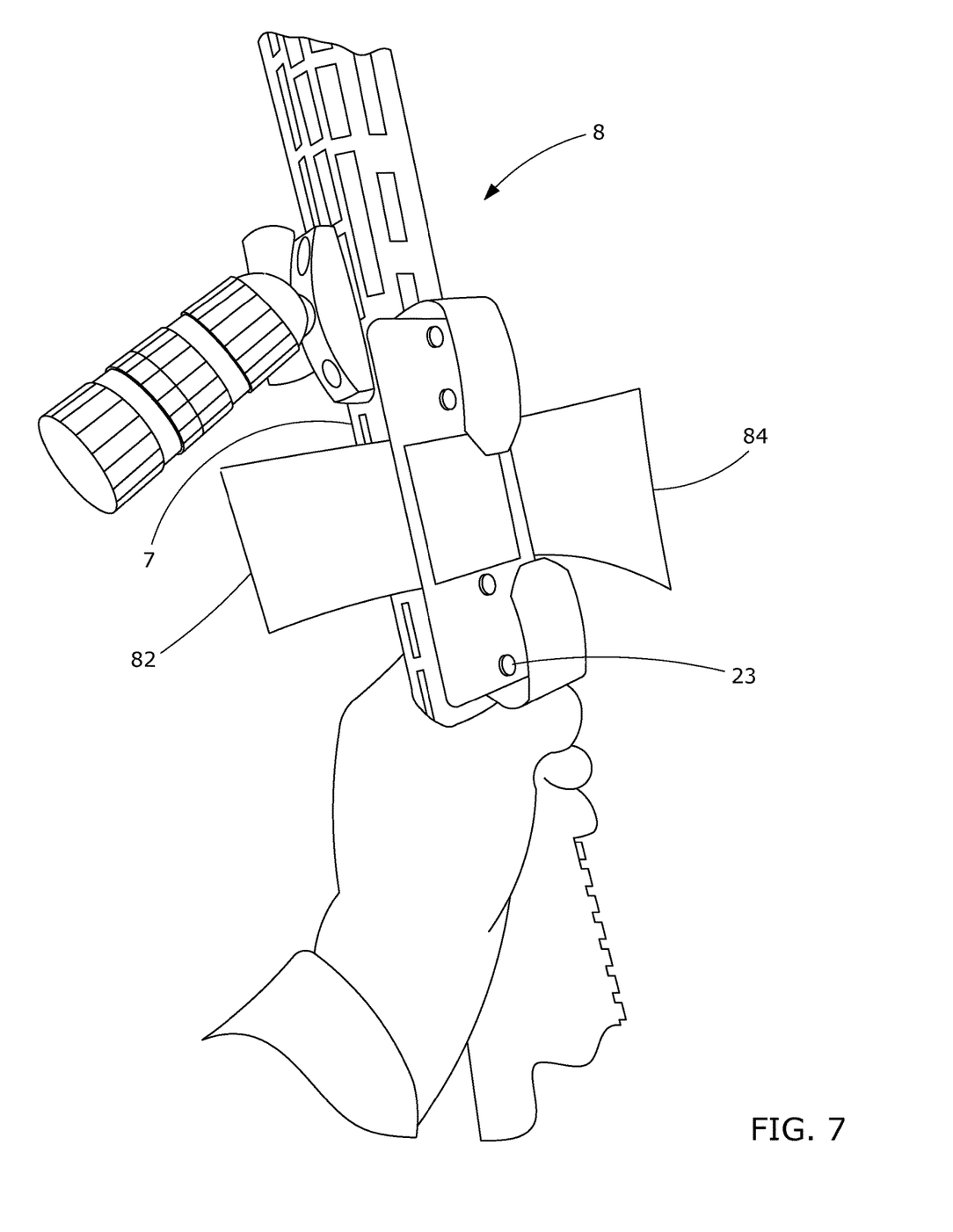
FIG. 7 is a view of the second embodiment of a tourniquet holder of FIG. 4 with the retention strap open and the tourniquet holder engaged with an associated weapon being grasped by an associated hand of an associated user.
Figure 8:
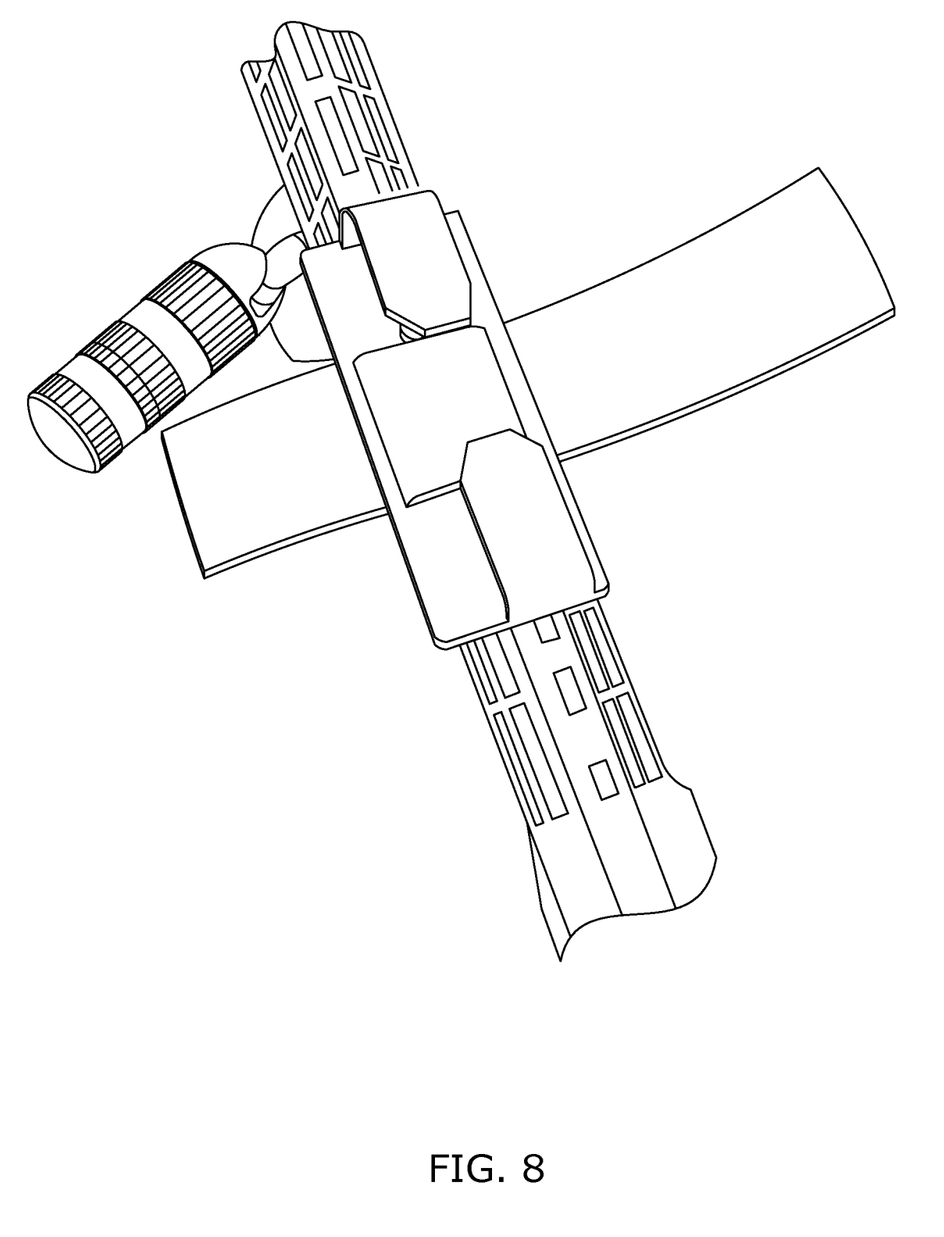
FIG. 8 is a view of the second embodiment of a tourniquet holder of FIG. 4 with the retention strap open and the tourniquet holder engaged with an associated weapon.
Figure 9:
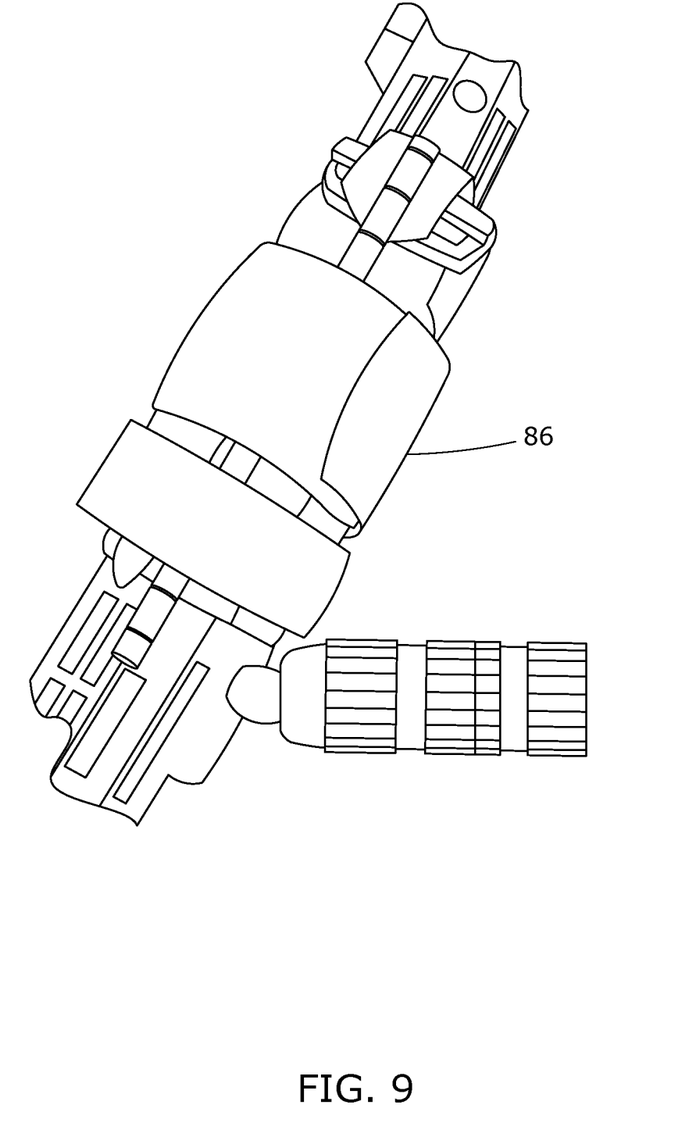
FIG. 9 is a view of the second embodiment of a tourniquet holder of FIG. 4 the retention strap closed and retaining a tourniquet, the tourniquet holder engaged with an associated weapon.
Figure 10:
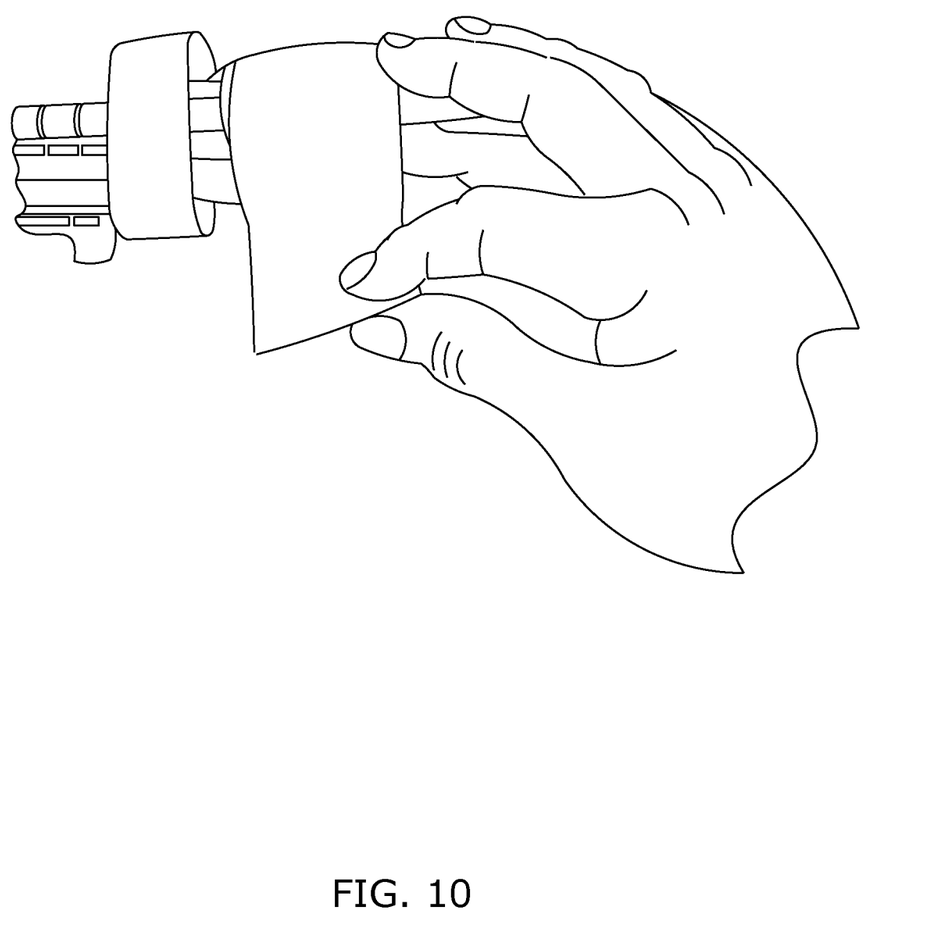
FIG. 10 is a view of the second embodiment of a tourniquet holder of FIG. 9 with the retention strap in the process of being opened to remove the retained tourniquet.
Figure 11:
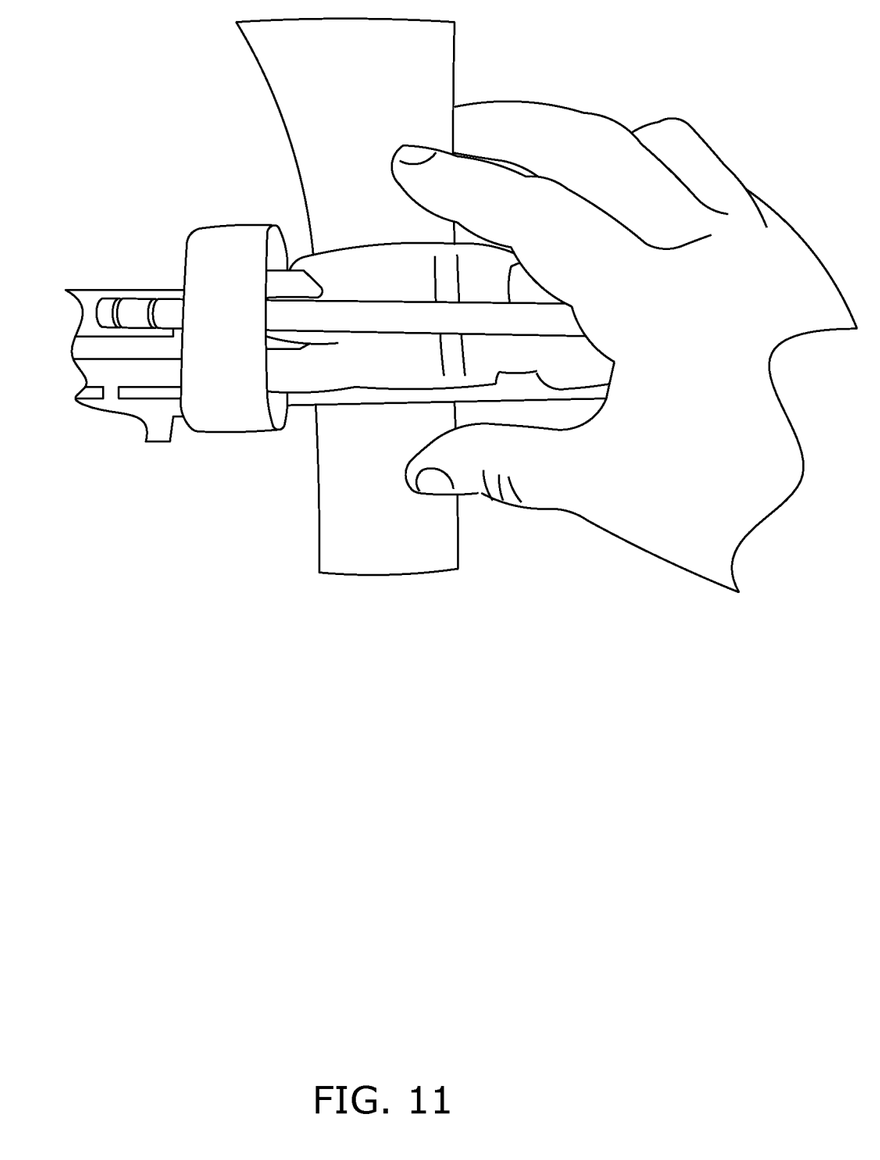
FIG. 11 is a view of the second embodiment of a tourniquet holder of FIG. 9 with the retention strap opened to permit the removal of the tourniquet.
Figure 12:
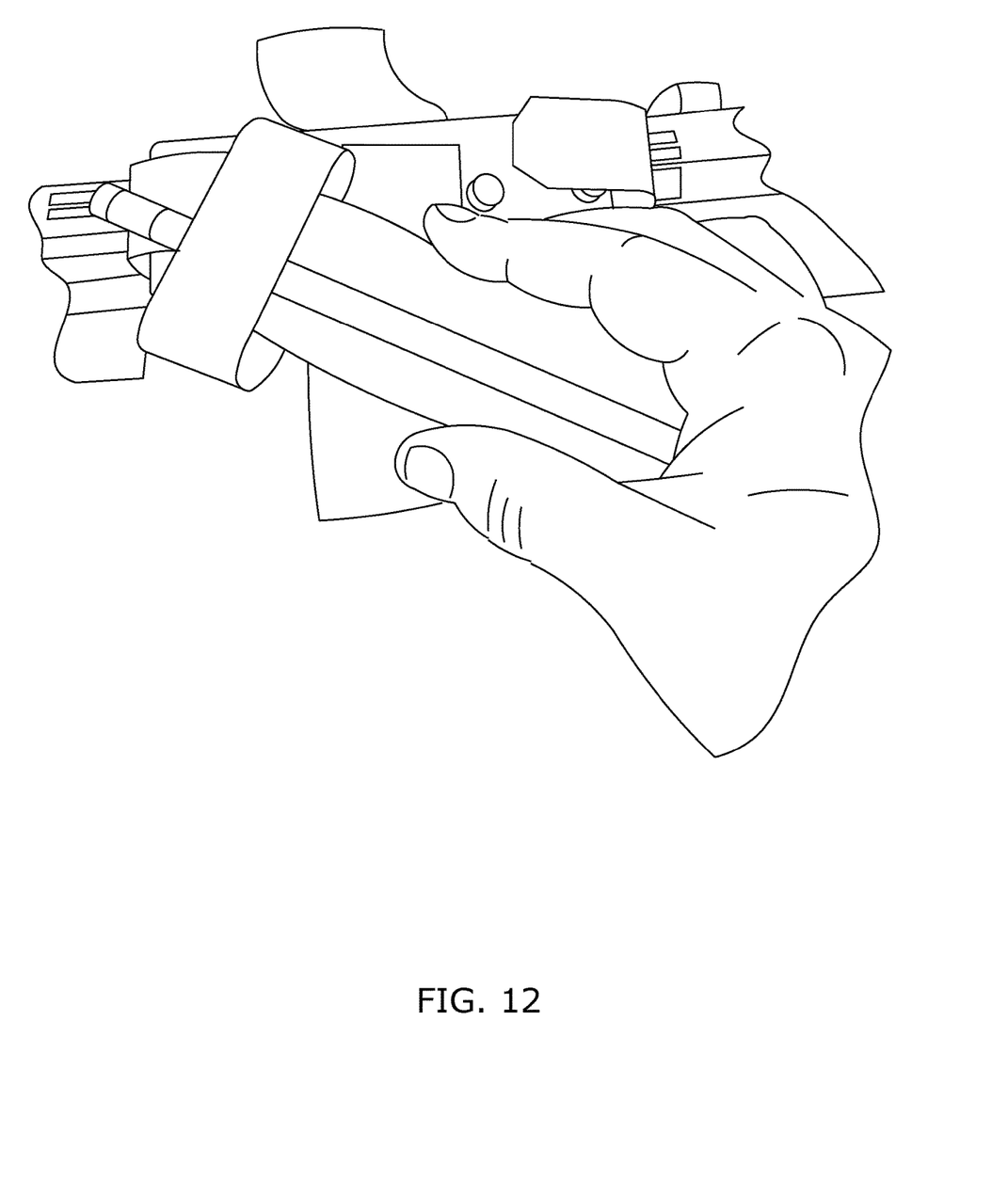
FIG. 12 is a view of the second embodiment of a tourniquet holder of FIG. 9 with the retention strap opened and the retained tourniquet in the process of being removed.
Figure 13:
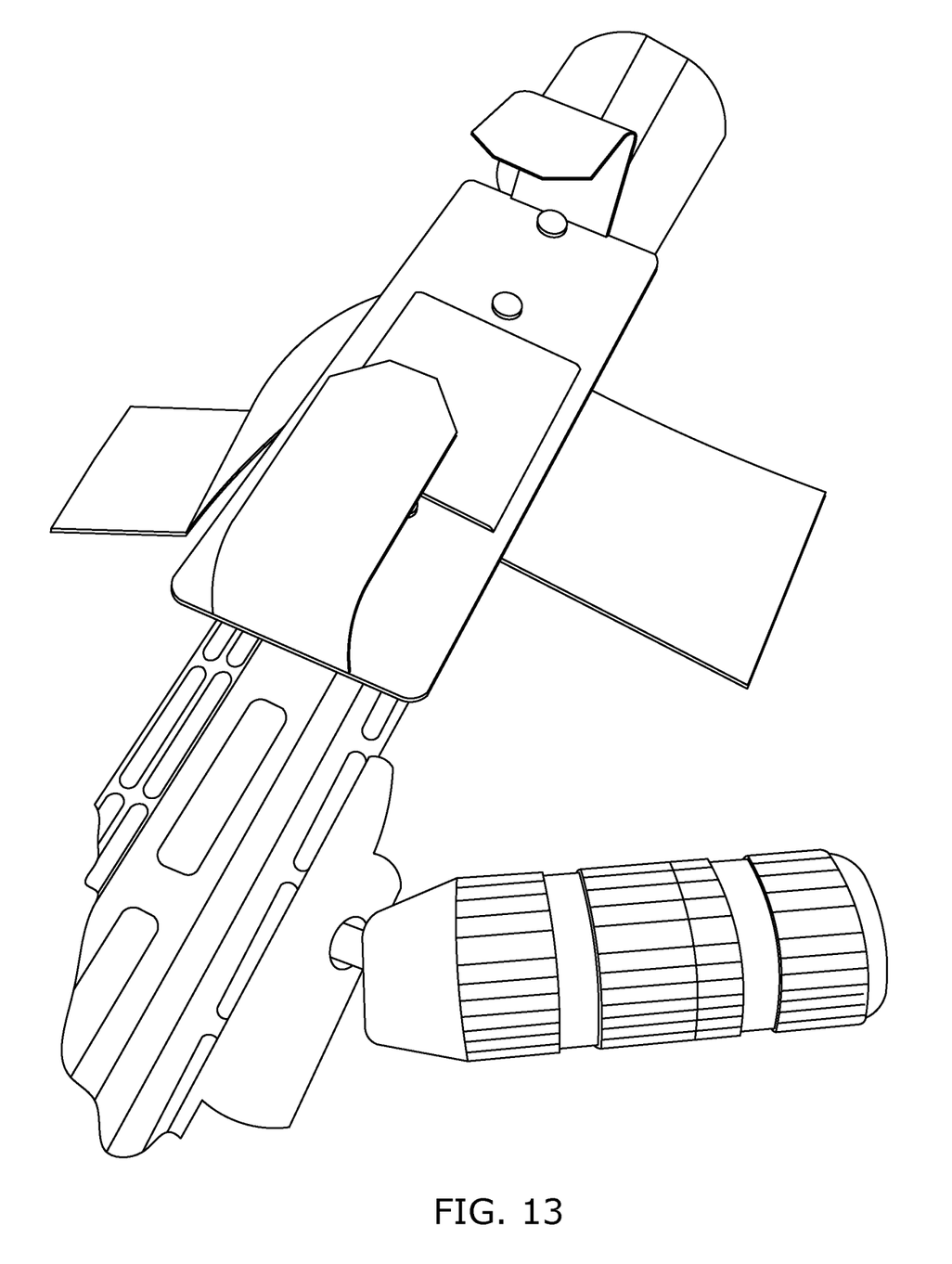
FIG. 13 is a view of the second embodiment of a tourniquet holder of FIG. 9 with the retention strap opened.

Referring now to FIGS. 2-3, the tourniquet holder 10 comprises a mounting base 20 adapted to be operationally engaged with a handguard 7 of an associated weapon 8, a first tang 40, a second tang 60, and an elongated retention strap 80.

In the first non-limiting embodiment the mounting base 20 may be a substantially flat plate 22 defining a first base face 24, and a second base face 26 facing oppositely from said first base face 24, with the second base 26 face offset from said first base face by a base thickness 28. In the first non-limiting embodiment the mounting base 20, the flat plate may be substantially rectangular with the flat plate 22 having a first base side edge 31 and a second base side edge 32 opposite said first base side edge 31 and offset from said first base side edge 31 by a base width 33, and further having a base top edge 35 and a base bottom edge 36 offset from said base top edge 35 by a base height 37. In other acceptable non-limiting embodiments of the mounting base 20, the flat plate 22 may be substantially square, or hexagonal or octagonal or other shape chosen with good engineering judgment.

In the first non-limiting embodiment the mounting base 20 may comprise one or more fastener apertures 21 adapted to operationally engage with a mechanical fastener 23, each said mechanical fastener 23 being further adapted to operationally engage with said handguard 7. The mechanical fasteners 23 may be any fastener chosen with good engineering judgment but in some non-limiting embodiments are Picatinny, M-lok, or KeyMod.

In the first non-limiting embodiment the mounting base 20 may comprise a retention slot 29 or two or more retention slots 29, such as a first retention slot 29A and a second retention slot 29B.

The first tang 40 may extend in a direction substantially normal to the first base face 24. In the non limiting embodiments shown in FIGS. 2-13, first tang 40 extends outwardly from first base face 24 and also may curve or otherwise extend over first base face 24.

The second tang 60 may extend in a direction substantially normal to the first base face 24. In the non limiting embodiments shown in FIGS. 2-13, second tang 60 extends outwardly from first base face 24 and also may curve or otherwise extend over first base face 24.

In the non limiting embodiments shown in FIGS. 2-13, first tang 40 and second tang 60 may define therebetween a margin 50 adapted to accommodate therein an associated tourniquet 9.

In the non limiting embodiments shown in FIGS. 4-13 the tourniquet holder 10 may comprise an elongated retention strap 80. The retention strap 80 may be engaged with the mounting base 20 by passing through said one or more retention slots 29. The elongated retention strap 80 may have a first end 82 and a second end 84 opposite the first end 82. The second end 84 may be selectably engagable with the first end 82 to selectably define a loop 86. In one embodiment and without limitation, the first end 82 and the second end 84 each comprise parts of hook and loop fastener adapted to selectable fastent the first end 82 the second end 84 to form a loop 86. The loop 86 may be adapted to retain therein the associated tourniquet 9.

In some non limiting embodiments of the tourniquet holder 10, the second end 84 is optionally adapted for one-handed disengagement from said first end 82. In some embodiments in which the second end 84 is adapted for one-handed disengagement from said first end 82, the first end 82 and the second end 84 each comprise parts of hook and loop fastener.

In some non limiting embodiments, the tourniquet holder 10 is operationally engaged with the handguard 7 of an associated weapon 8. In some such embodiments, said weapon 8 is a rifle or a crossbow.

In some non limiting embodiments of the tourniquet holder 10, the first tang 40 is substantially adjacent to said base top edge 35.

In some non limiting embodiments of the tourniquet holder 10, the second tang 60 is substantially adjacent to said base bottom edge 36.

In some non limiting embodiments of the tourniquet holder 10, the fastener apertures 21 comprise a first fastener aperture 21A substantially adjacent to the first base side edge 31, and a second fastener aperture 21B substantially adjacent to the second base side edge 32.

In some non limiting embodiments of the tourniquet holder 10, the one or more retention slots 29 comprise a first retention slot 29A and a second retention slot 29B. In come embodiments comprising first retention slot 29A and second retention slot 29B, the elongated retention strap 80 passes through both said first retention slot 29A and said second retention slot 29B.

Also provided here is a method for using a tourniquet holder 10. One non-limiting method of using a tourniquet holder 10 comprises providing the above referenced first embodiment of a tourniquet holder 10, providing a weapon 8 with a handguard 7, providing a tourniquet 9, engaging the mounting base 20 of the tourniquet holder 10 with the handguard 7; and using the retention strap of the tourniquet holder 10 to retain the associated tourniquet 9.

It is to be understood that engagement of the tourniquet holder 10 is only one application of interest. It is also of interest that the tourniquet holder 10 be engaged with other instruments, vehicles, or structures. For example, a tree worker or other party may wish to have a tourniquet holder 10 engaged to a chain saw. A police officer, or emergency medical technician, or fireman might engage the tourniquet holder 10 with his personally carried gear, or might engage it at a handy location in his work vehicle. It would be possible to mount tourniquet holder 10 to desired instruments, vehicles, or structures by straps, mechanical fasteners, adhesives, or other means chosen with good engineering judgment. In some embodiments, removal of a tourniquet stored in a tourniquet holder 10 triggers an alarm, alert lamp, telephones an emergency contact, such as, in the US, 9-1-1, or otherwise activates a signal for medical aid.

Any of the features or attributes of the above described embodiments and variations can be used in combination with any of the other features and attributes of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A tourniquet holder comprising:
   A) a mounting base adapted to be operationally engaged with a handguard of an associated weapon, said mounting base having
      i) a substantially flat plate defining a first base face, and a second base face facing oppositely from said first base face, said second base face offset from said first base face by a base thickness, said plate further having a first base side edge and a second base side edge opposite said first base side edge and offset from said first base side edge by a base width, said plate further having a base top edge and a base bottom edge offset from said base top edge by a base height;
      ii) one or more fastener apertures adapted to operationally engage with a mechanical fastener, each said mechanical fastener being further adapted to operationally engage with said handguard,
      iii) one or more retention slots; and
   B) a first tang extending in a direction substantially normal to said first base face;
   C) a second tang extending in a direction substantially normal to said first base face;
   D) wherein said first tang and said second tang define therebetween a margin adapted to accommodate therein an associated tourniquet; and
   E) an elongated retention strap passing through said one or more retention slots, said elongated retention strap having a first end and a second end, said second end being selectably engagable with said first end to selectably define a loop, said loop being adapted to retain therein said associated tourniquet.

2. The tourniquet holder of claim 1, wherein said second end is adapted for one-handed disengagement from said first end.

3. The tourniquet holder of claim 1, wherein said weapon is a rifle.

4. The tourniquet holder of claim 1, wherein said first tang is substantially adjacent to said base top edge.

5. The tourniquet holder of claim 1, wherein said second tang is substantially adjacent to said base bottom edge.

6. The tourniquet holder of claim 1, wherein said one or more fastener apertures comprises a first fastener aperture substantially adjacent to the first base side edge.

7. The tourniquet holder of claim 6, wherein said one or more fastener apertures comprises a second fastener aperture substantially adjacent to the second base side edge.

8. The tourniquet holder of claim 7, wherein said one or more retention slots comprise a first retention slot and a second retention slot.

9. The tourniquet holder of claim 8, wherein said elongated retention strap passes through both said first retention slot and said second retention slot.

10. A method for using a tourniquet holder comprising:
   A) providing a tourniquet holder having
      i) a mounting base adapted to be operationally engaged with a handguard of an associated weapon, said mounting base having
         a) a substantially flat plate defining a first base face, and a second base face facing oppositely from said first base face, said second base face offset from said first base face by a base thickness, said plate further having a first base side edge and a second base side edge opposite said first base side edge and offset from said first base side edge by a base width, said plate further having a base top edge and a base bottom edge offset from said base top edge by a base height;
         b) one or more fastener apertures adapted to operationally engage with a mechanical faster, each said mechanical fastener being further adapted to operationally engage with said handguard,
         c) one or more retention slots, and
      ii) a first tang extending in a direction substantially normal to said first base face,
      iii) a second tang extending in a direction substantially normal to said first base face,
      iv) wherein said first tang and said second tang define therebetween a margin adapted to accommodate therein an associated tourniquet,
      v) an elongated retention strap passing through said one or more retention slots, said elongated retention strap having a first end and a second end, said second end being selectably engagable with said first end to selectably define a loop, said loop being adapted to retain therein said associated tourniquet; and
   B) providing a weapon having a handguard;
   C) providing a tourniquet;
   D) engaging said mounting base with the handguard; and
   E) using said retention strap to retain said tourniquet.

* * * * *